United States Patent
Ishikura et al.

(10) Patent No.: US 6,304,323 B1
(45) Date of Patent: Oct. 16, 2001

(54) METHOD FOR DETECTING DEFECT IN BOTTLE

(75) Inventors: Tohru Ishikura; Hiroyuki Fukuchi; Yasuo Miwa, all of Yokohama (JP)

(73) Assignee: Kirin Techno-System Corporation, Yokohama (JP)

( * ) Notice: Subject to any disclaimer, the term of this patent is extended or adjusted under 35 U.S.C. 154(b) by 0 days.

(21) Appl. No.: 09/450,722

(22) Filed: Nov. 30, 1999

(30) Foreign Application Priority Data

Nov. 30, 1998 (JP) .................................. 10-340400
Nov. 30, 1998 (JP) .................................. 10-340401

(51) Int. Cl.[7] .................................. G01N 21/00
(52) U.S. Cl. .................... 356/239.4; 356/240.1; 356/239.6; 250/223 B
(58) Field of Search .............. 356/239.4, 239.5, 356/239.6, 240.1; 250/223 B, 225, 562, 572; 358/106

(56) References Cited

U.S. PATENT DOCUMENTS

| 4,376,951 | * | 3/1983 | Miyazawa | 250/223 B |
| 4,679,075 | * | 7/1987 | Williams et al. | 356/239.4 |
| 4,701,612 | * | 10/1987 | Sturgill | 356/240.1 |
| 4,831,250 | * | 5/1989 | Fukuchi et al. | 356/239.4 |
| 4,983,822 | * | 1/1991 | Fukuchi | 356/239.4 |
| 5,004,909 | * | 4/1991 | Fukuchi | 356/239.5 |
| 5,059,031 | * | 10/1991 | Hamel et al. | 356/240.1 |
| 5,471,297 | | 11/1995 | Tani . | |

FOREIGN PATENT DOCUMENTS 0 344 617   12/1989   (EP) .
0 491 555    6/1992   (EP) .

* cited by examiner

Primary Examiner—Richard A. Rosenberger
Assistant Examiner—Sang H. Nguyen
(74) Attorney, Agent, or Firm—Oblon, Spivak, McClelland, Maier & Neustadt, P.C.

(57) ABSTRACT

The present invention relates to a method for detecting a defect in a barrel portion of a bottle. The defect in the barrel portion of the bottle includes a thin blister and a longitudinal streak. The defect in the bottle barrel is detected by imaging the bottle barrel with a CCD camera based on light which has passed through a light shield plate having a plurality of oblique slits and the bottle barrel, and processing the image of the bottle barrel generated by the CCD camera to determine whether or not the defect is present.

2 Claims, 8 Drawing Sheets

F I G. 3
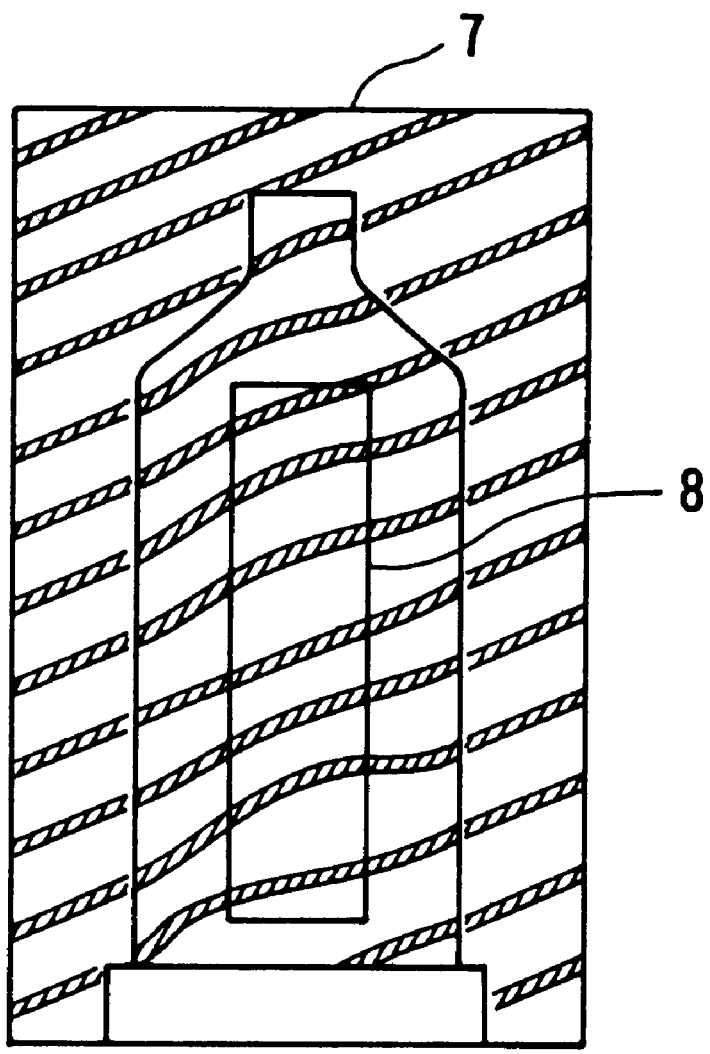

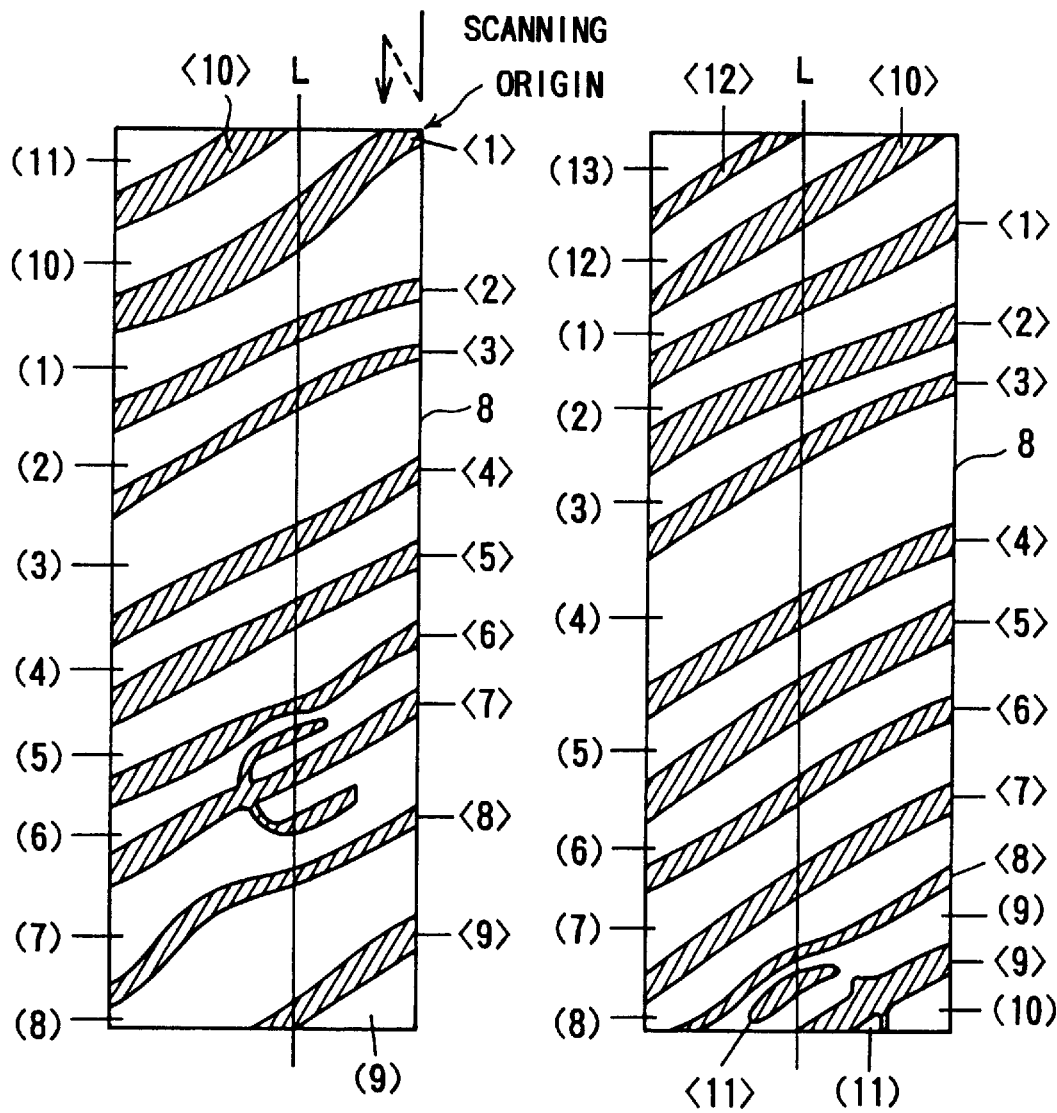

METHOD FOR DETECTING DEFECT IN BOTTLE

BACKGROUND OF THE INVENTION

1. Field of the Invention

The present invention relates to a method for detecting a defect in a bottle based on an imaging technology, and more particularly to a method for detecting a refractive defect in a barrel portion of the bottle.

2. Description of the Related Art

Defects in a barrel portion of a glass bottle are classified into shading defects which block applied light to prevent the light from passing therethrough and refractive defects which refract applied light. The applicant of the present application has proposed a method of detecting both shading defects and refractive defects as disclosed in Japanese patent publication No. 6-90150. According to the disclosed method, a light shield plate (referred to as an obliquely slit plate in the specification) having a plurality of oblique slits is positioned between a source of diffused light and a bottle under test. Diffused light from the source passes through the light shield plate and the barrel portion of the bottle, producing an image of a striped pattern. The image of the striped pattern is scanned to compare the levels of brightness at three closely positioned spots in the image for flaw detection.

If the bottle suffers large wall thickness variations, then the striped pattern tends to be so irregular that it is difficult to detect defects in the barrel portion of the bottle. The inventors of the present invention have made efforts to develop a method of processing images of irregular striped patterns particularly for the detection of thin blisters among different types of blisters which are one kind of refractive defects. The thin blister refers to a blister in the form of a thin lens on a surface of the glass bottle or in the glass bottle.

Further, the inventors of the present invention have made efforts to develop a method of processing images of irregular striped patterns particularly for the detection of longitudinal streaks. The longitudinal streak refers to a linear recess that appears partly in the longitudinal direction of the bottle.

SUMMARY OF THE INVENTION

It is therefore a first object of the present invention to provide a method for detecting a defect, which is referred to as a thin blister, in a barrel portion of a bottle.

It is a second object of the present invention to provide a method for detecting a defect, which is referred to as a longitudinal streak, in a barrel portion of a bottle.

In order to accomplish the first object, according to a first aspect of the present invention, there is provided a method for detecting defect in bottle, comprising: imaging a barrel portion of a bottle with a CCD camera based on light which has passed through a light shield plate having a plurality of oblique slits and the barrel portion; generating a binary image having a striped pattern of bright and dark areas within a window having a certain area from an image of the barrel portion generated by the CCD camera; scanning the binary image in a longitudinal direction of the barrel portion to generate a labeled image in which labels are assigned to the bright and dark areas of the striped pattern, respectively; and scanning the labeled image in a longitudinal direction of the barrel portion to determine a defect in the barrel portion if there is a label which is not in contact with any one of sides of the window or if one label appears more than a preset number of times along a scanning line.

With the above method, the barrel portion of the bottle is imaged by the CCD camera, and a generated image of a striped pattern is processed into a binary image having a striped pattern of bright and dark areas. In the binary image, a defect in the form of a thin blister is represented by an image of branched stripes or an isolated stripe. Then, a labeled image in which labels are assigned to the bright and dark areas of the striped pattern is produced from the binary image. Thereafter, the labeled image is scanned to determine an image of branched stripes or an isolated stripe for thereby detecting a thin blister if there is a label which is not in contact with any one of sides of the window or if one label appears more than a preset number of times along a scanning line.

In order to accomplish the second object, according to a second aspect of the present invention, there is provided a method for detecting defect in bottle, comprising: imaging a barrel portion of a bottle with a CCD camera based on light which has passed through a light shield plate having a plurality of oblique slits and the barrel portion; generating a binary image having a striped pattern of bright and dark areas within a window having a certain area from an image of the barrel portion generated by the CCD camera; scanning the binary image in a longitudinal direction of the barrel portion to determine the number of successive bright or dark pixels along a first scanning line; determining the number of area-changing points where a bright area changes to a dark area or a dark area changes to a bright area between a start point and an end point of pixels which are equal to the successive pixels whose number has exceeded the first preset number along the first scanning line, along a second scanning line which precedes the first scanning line by a second preset number, if the determined number of successive bright or dark pixels exceeds a first preset number; and determining the presence of a defect if the determined number of area-changing points is equal to or greater than a third preset number.

With the above method, the barrel portion of the bottle is imaged by the CCD camera, and a generated image of a striped pattern is processed into a binary image having a striped pattern of bright and dark areas. In the binary image, a defect in the form of a longitudinal streak is represented by a longitudinal succession of bright or dark pixels. The number of successive bright or dark pixels along a first scanning line (L) is determined from the binary image. If the determined number of successive bright or dark pixels exceeds a first preset number (K1), then the number of area-changing points where a bright area changes to a dark area or a dark area changes to a bright area is determined between a start point and an end point of pixels which are equal to the successive pixels whose number has exceeded the first preset number (K1) along the first scanning line (L), along a second scanning line (L') which precedes the first scanning line (L) by a second preset number (K2). If the determined number of area-changing points is equal to or greater than a third preset number (K3), then the distance between adjacent stripes along the second scanning line (L') is normal, and a defect in the form of a longitudinal streak is present along the first scanning line (L). If the determined number of area-changing points is smaller than the third preset number (K3), then the distance between adjacent stripes along the first and second scanning lines (L and L') is normal, and a defect in the form of a longitudinal streak is not present along the first and second scanning lines (L and L').

The above and other objects, features, and advantages of the present invention will become apparent from the following description when taken in conjunction with the accompanying drawings which illustrate a preferred embodiment of the present invention by way of example.

BRIEF DESCRIPTION OF THE DRAWINGS

FIG. 3 is a view showing an image of a bottle produced by a CCD camera of the inspection apparatus shown in FIG. 1;

FIGS. 5A and 5B are views of images which have been labeled;

DETAILED DESCRIPTION OF THE PREFERRED EMBODIMENT

A method for detecting defect in bottle according to a first embodiment of the present invention will be described with reference to FIGS. 1 through 10.

Figure 1:
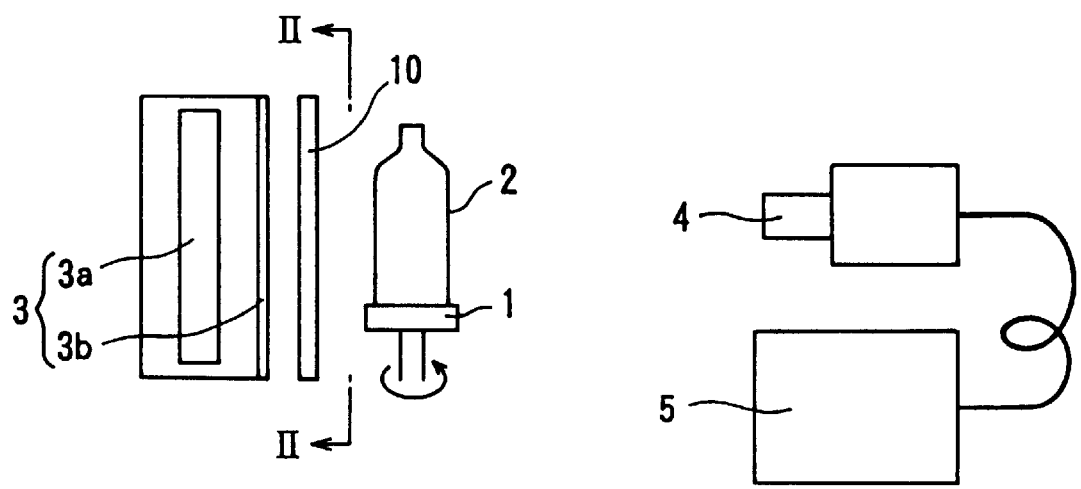
FIG. 1 is a front elevational view of an inspection apparatus for carrying out a method for detecting a defect in a barrel portion of a bottle according to a first embodiment of the present invention.

As shown in FIG. 1, an inspection apparatus for carrying out a method for detecting a defect in a barrel portion of a bottle comprises a diffused light source 3 for emitting diffused light and applying the diffused light to a glass bottle 2 placed on a turntable 1, a light shield plate 10 disposed between the diffused light source 3 and the glass bottle 2 and having a plurality of oblique slits, a CCD (Charge-Coupled Device) camera 4 positioned on one side of the glass bottle 2 remotely from the diffused light source 3 for imaging the glass bottle 2 from one side thereof, i.e., horizontally, and an image processor 5 for processing an image of the glass bottle 2 which has been generated by the CCD camera 4. The diffused light source 3 comprises a light source 3a and a light diffuser plate 3b. An optical axis of the CCD camera 4 is horizontal or substantially horizontal.

Figure 2:
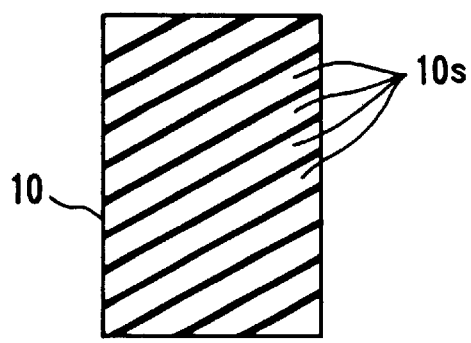
FIG. 2 is a view taken along line II–II of FIG. 1 and showing a light shield plate.

FIG. 2 shows the light shield plate 10 which has a plurality of oblique slits 10s.

While the glass bottle 2 is being rotated about its vertical axis by the turntable 1, the CCD camera 4 images the glass bottle 2 from one side thereof to generate a number of images thereof. When diffused light emitted from the diffused light source 3 is applied through the slits 10s in the light shield plate 10 to the glass bottle 2, a part of the applied light passes through the glass bottle 2 and reaches the CCD camera 4.

Figure 4A:
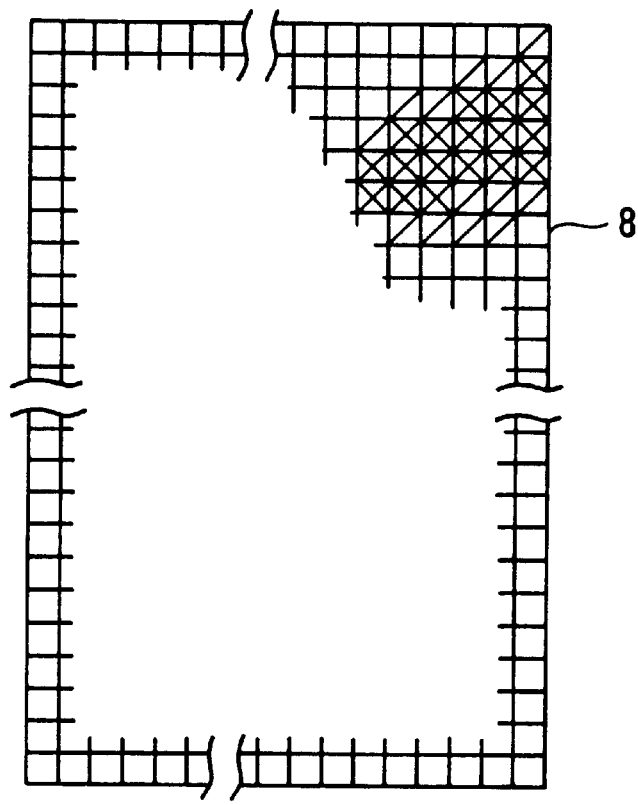
FIG. 4A is a fragmentary view of an original image of a barrel portion of the bottle produced by the CCD camera.
Figure 4B:
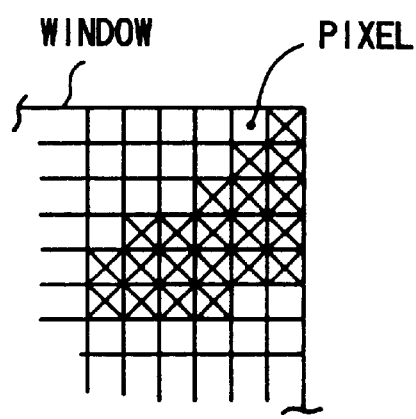
FIG. 4B is an enlarged fragmentary view of a binary image generated from the original image shown in FIG. 4A.

FIG. 3 shows an image of the glass bottle 2 which has been generated by the CCD camera 4. As shown in FIG. 3, when the barrel portion of the glass bottle 2 is imaged by the CCD camera 4 with light that has passed through the light shield plate 10, an image 7 containing a striped pattern is generated by the CCD camera 4. Since the glass bottle 2 has wall thickness variations or irregularities, the striped pattern is deformed in some parts thereof. A window 8 is established centrally in the image 7, and image data in the window 8 is processed by the image processor 5. Specifically,, the image processing by the image processor 5 is carried out as follows:

The image processing is composed of a number of steps. In step 1, a binary image is generated from the striped pattern in the window 8 of the image 7. FIG. 4A shows an original image, in the window 8 produced by the CCD camera 4, and FIG. 4B shows a binary image generated from the original image shown in FIG. 4A. As shown in FIG. 4A, the original image in the window 8 includes a dark light-shielded area (indicated by "x" in square pixels), a bright light-transmitted area (indicated by blank square pixels), and boundary areas (indicated by "/" in square pixels) which are of an intermediate shade between the dark and bright areas. When the brightness data of the pixels are converted into binary data using a threshold representing a certain level of brightness, those pixels which are brighter than the threshold become bright pixels (represented by 1, for example), and those pixels which are darker than the threshold become dark pixels (represented by 0, for example). Therefore, the image represented by the binary data comprises a matrix of data "1" and "0". A change from the bright area to the dark area of the original image is equivalent to a change from the data "1" to the data "0" of the binary image. In FIG. 4B, the blank square pixel has the bright data "1", and the square pixel marked with "x" has the dark data "0".

In step 2, the binary image in the window 8 generated in step 1 is scanned in a vertical direction of the glass bottle 2 to label bright areas and dark areas of the striped pattern.

FIGS. 5A and 5B show images which have been labeled in step 2. In each of FIGS. 5A and 5B, the image is scanned downwardly from the origin at an upper right corner thereof, and scanned horizontally from the right to the left.

A thin blister, which is a type of defect contained in the glass bottle 2, is represented by an image of plural stripes. In the original image captured by the CCD camera 4, part of the plural stripes has an intermediate shade between dark and bright areas. In the binary image, therefore, depending on the brightness in the original image, the thin blister is represented by an image of joined and branched stripes as indicated by <7> in FIG. 5A or an image of an isolated stripe which is not in contact with the window 8 as indicated by <11> in FIG. 5B. While the images shown in FIGS. 5A and 5B are given for illustrative purpose, the images of thin blisters are characterized in that part of stripes is branched or isolated. This is because the thin blister has a lens effect by which an incident light is refracted more intensely than the normal portion. Therefore, depending on the degree of refraction, the thin blister converges light to cause a whole area corresponding to the thin blister to become a bright area in the binary image, or the thin blister forms image of small slits thereon to cause areas corresponding to the image of small slits to become dark areas in the binary image. The defect detecting method according to the present invention is based on the extraction of such a feature.

In step 2 the binary image is labeled by scanning the binary image to detect continuity of the stripes and assign identification numbers to the bright areas and the dark areas. One area is composed of pixels having the same identification number. The labeling is carried out by labeling with 8-neighbours. In FIGS. 5A and 5B, labels are represented by <1>, <2>, ..., <10>(in FIG. 5A) or <12>(in FIG. 5B) for dark areas, and (1), (2), ..., (11) (in FIG. 5A) or (13) (in FIG. 5B) for bright areas. When focusing on the dark area, the labeled image is composed of dark areas <1>, <2>, ..., <10> and bright areas 0 (bright areas are assumed to be denoted by 0). When focusing on the bright area, the labeled image is composed of bright areas (1), (2), ..., (11) (in FIG. 5A) or (13) (in FIG. 5B) and dark areas 0 (dark areas are assumed to be denoted by 0). These two kinds of images are generated.

In step 3, the labeled images produced in step 2 are scanned in the longitudinal direction thereof, and a defect is determined to be present in the bottle if a label that is not in contact with either one of the four sides of the window 8 is present or if one label appears more than a preset number of times along a scanning line. Specifically, when the image of the dark labels is scanned in FIG. 5B, a label <11> that is not in contact with either one of the four sides of the window 8 is present on or near a scanning line L, and hence the presence of a defect is determined. Since the label <11> is not present in either one of the four sides of the window 8 when the image is scanned, it is determined that the label <11> is not in contact with either one of the four sides of the window 8.

Figure 6:
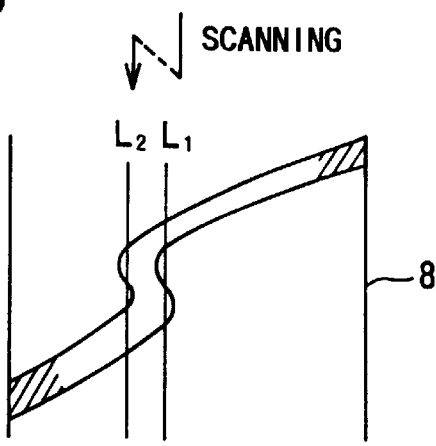
FIG. 6 is a fragmentary view of an image which has been labeled.

When the image of the bright labels is scanned in FIG. 5B, the label (9) appears twice on or near the scanning line L. When the image of the dark labels is scanned in FIG. 5A, the label <7> appears three times on or near the scanning line L. When the image of the bright labels is scanned in FIG. 5A, the label (6) appears twice on or near the scanning line L, and the label (7) also appears twice on or near the scanning line L. Depending on wall thickness variations of the bottle, a substantially S-shaped stripe may appear as shown in FIG. 6 though it does not represent a defect. When the image shown in FIG. 6 is scanned, one label appears twice along each of scanning lines $L_1$ and $L_2$. If the preset number of times for determining the appearance of one label is "2", then since the label <7> appears three times in FIG. 5A, it can be distinguished from the substantially S-shaped stripe (which is not a defect) shown in FIG. 6, and can be determined as a defect.

Images in which bright areas and dark areas of striped patterns are labeled, respectively are generated because one label appears different numbers of times for bright areas and dark areas, and the appearance of one label by a greater number of times is to be recognized. In FIG. 5A, the label (6) or (7) appears twice, and the label <7> appears three times. However, the label (6) or (7) may appear three times, and the label <7> may appear twice. While the preset number of times for determining the appearance of one label is "2" in the illustrated embodiment, it is not limited "2" because images change from bottle to bottle. The preset number of times for determining the appearance of one label is determined based on the results of many sample tests.

Figure 7:
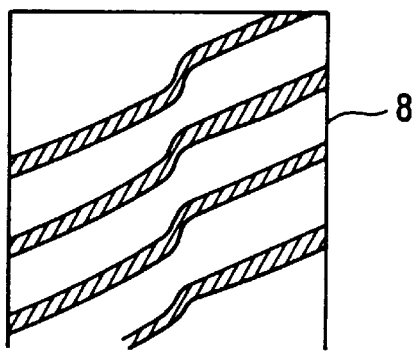
FIG. 7 is a fragmentary view of a binary image of the barrel portion including a seam line.
Figure 8A:
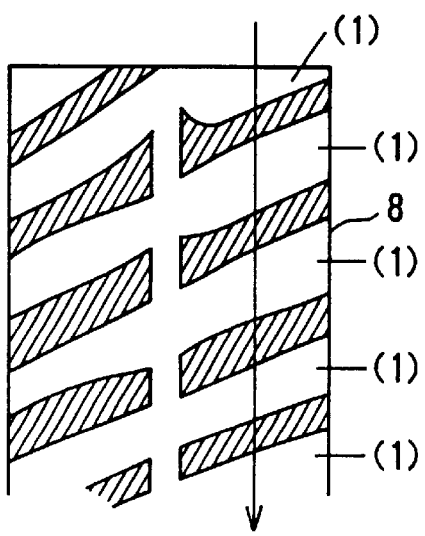
FIGS. 8A and 8B are fragmentary views of binary images of the barrel portion including the seam line.
Figure 8B:
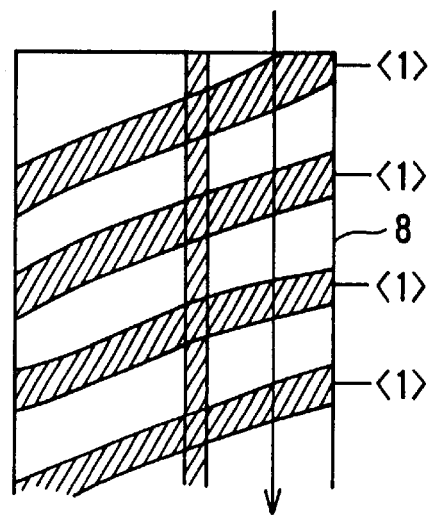

There is one phenomenon which should be taken into account in carrying out the method according to the present invention. A glass bottle has a vertical ridge referred to "seam line". Some bottles have gentle ridges, and some bottles have sharp ridges. FIGS. 7, 8A, and 8B fragmentarily show binary images of the barrel portion of the bottle including the seam line in the window 8. If the vertical ridge of the seam line of the bottle barrel is gently protrusive, then stripes are continuous as shown in FIG. 7, and the method of the present invention is directly applicable to the bottle barrel. If the vertical ridge of the seam line of the bottle barrel is sharply protrusive, then bright areas and dark areas are interrupted as indicated by images shown in FIGS. 8A and 8B. Whether the image shown in FIG. 8A or the image shown in FIG. 8B is generated depends on the threshold used to convert the brightness data of the original image into binary data. In FIGS. 8A and 8B, since one label appears more than the preset number of times, the seam line is determined as a defect. To avoid the determination of the seam line as a defect, it is necessary to mask the image of the seam line, i.e., to keep the seam line out of the defect detecting process.

Figure 9:
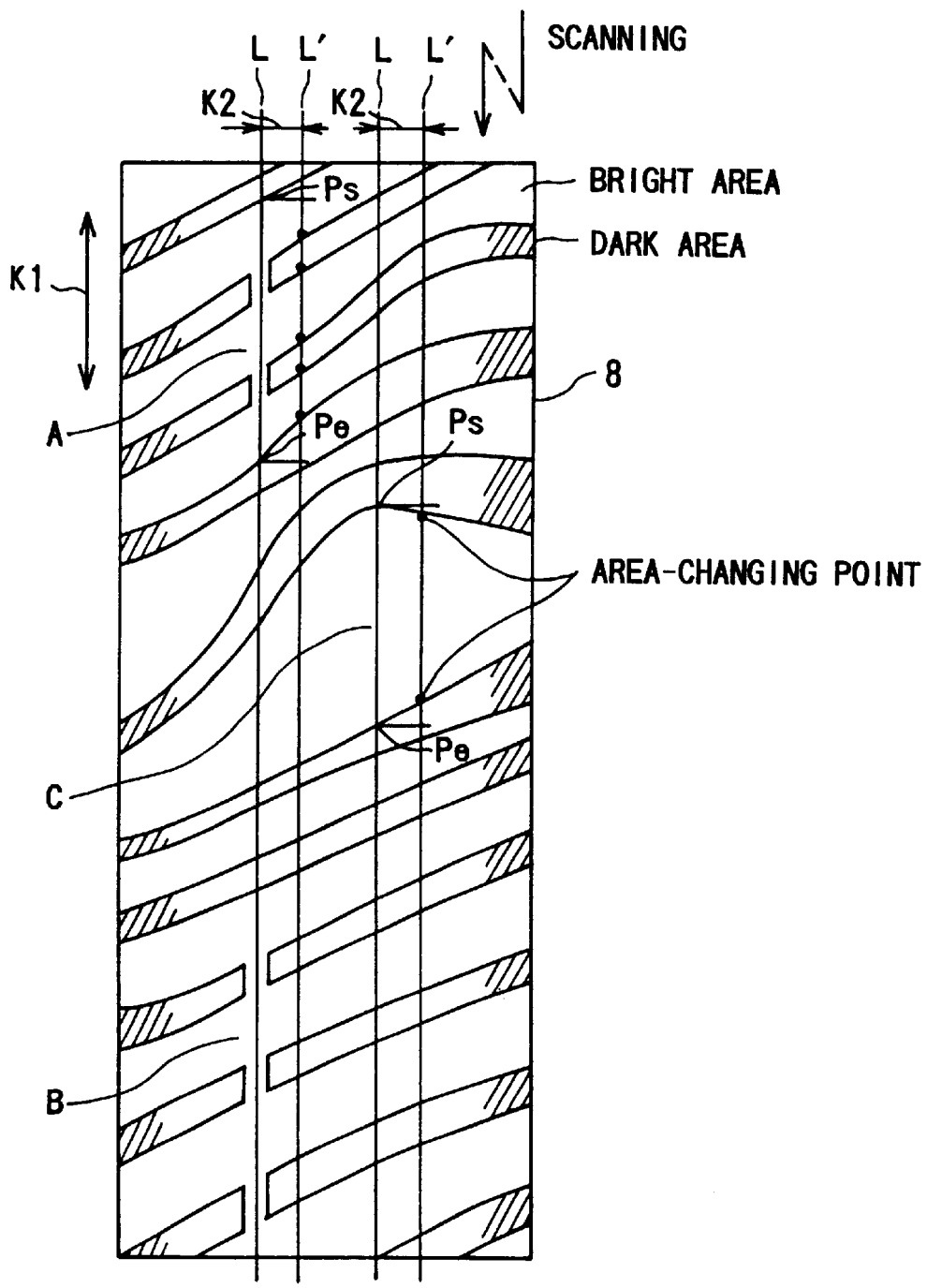
FIG. 9 is a view of a binary image of the barrel portion including the seam line.
Figure 10:
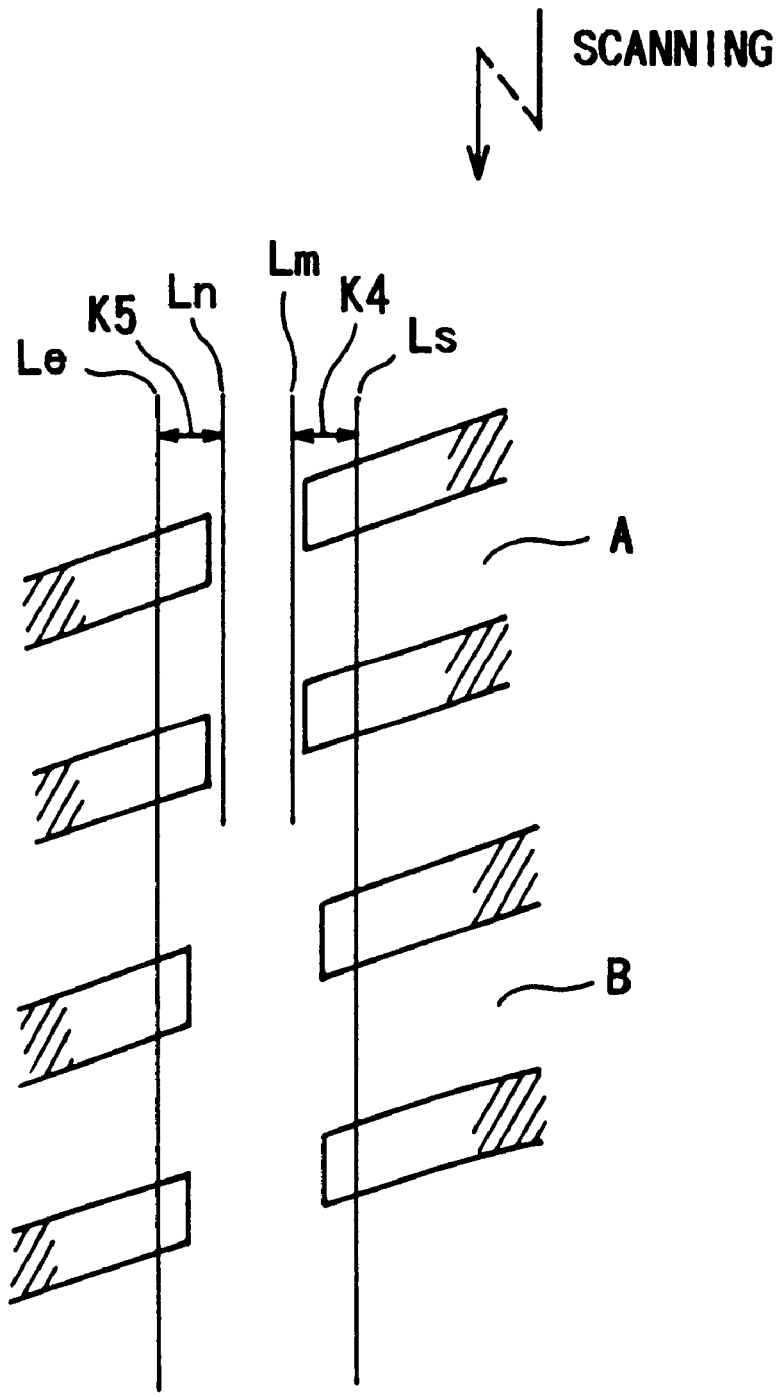
FIG. 10 is a fragmentary view of a binary image of the barrel portion including the seam line.

FIG. 9 shows a binary image including a portion of the seam line. In FIG. 9, dark areas are shown hatched only in edge portions, but not in a central portion, of the window 8 for the convenience of illustration, and A and B represent an area corresponding to the seam line in the window 8. FIG. 10 shows the area A and B as being positioned adjacent to each other.

A process of masking the area A and B corresponding to the seam line will be described below with reference to FIGS. 9 and 10. In step S1, the binary image is scanned in the longitudinal direction of the bottle to determine the number of successive pixels in bright or dark areas along a scanning line L. Then, in step S2, if the number of successive pixels determined in step S1 exceeds a preset number K1, then along a scanning line L' that precedes the scanning line L by a preset number K2, the number of area-changing points where a bright area changes to a dark area or a dark area changes to a bright area is determined between a start point Ps and an end point Pe of pixels which are equal to the successive pixels whose number has exceeded the preset number K1 along the scanning line L. In step S3, if the number of area-changing points is equal to or greater than a preset number K3, then the number of the scanning line L is stored. In step S4, an image extending from a scanning line Ls that precedes, by a preset number K4, a scanning line Lm whose number was the first number stored in step S3 to a scanning line Le that precedes, by a preset number K5, a scanning line Lm whose number was the last number stored in step S3, is masked.

If there is a scanning line L along which there are successive pixels in excess of the ordinary gap between adjacent stripes in step S1, then a seam line is present along the scanning line L. However, as indicated by an area C in FIG. 9, there is an instance where bright pixels are successively present as with the area A though no seam line is actually present in the area C. Therefore, in step S2, the number of area-changing points where a bright area changes to a dark area or a dark area changes to a bright area is determined along the scanning line L' that precedes the scanning line L by a certain number. In step S3, the areas A, C are distinguished from each other by determining whether or not the number of area-changing points is equal to or greater than the preset number K3. In FIG. 9, the number of area-changing points in the area A is 5, and the number of area-changing points in the area C is 2. If the preset number K3 is 3, then the area A corresponding to the seam line and the area C are distinguished from each other.

As shown in FIGS. 9 and 10, if there is an area corresponding to the seam line in the image, then bright or dark areas in a binary image containing the seam line are horizontally interrupted by the area corresponding to the seam line. The bright or dark areas may be interrupted over different distances. In FIG. 10, the bright or dark areas are interrupted over different distances by the areas A, B, with the interrupted distance in the area B being greater than the interrupted distance in the area A. Therefore, in step S4, as shown in FIG. 10, the image extending from the scanning line Ls that precedes, by the preset number K4, the scanning line Lm whose number was the first number for the determined seam line to the scanning line Le that precedes, by the preset number K5, the scanning line Lm whose number was the last number for the determined seam line, is masked. In this manner, the image of the interrupted areas is masked to keep the seam line out of the defect detecting process.

Since binary images generated from bottles vary from bottle to bottle, the preset numbers K1 through K5 are determined as the results of many sample tests, and may be changed if necessary.

The method for detecting defect in bottle according to the first embodiment of the present invention is capable of reliably detecting thin blisters in the bottle barrel as it extracts features of stripe irregularities in binary images of the bottle which are caused by the thin blisters.

Next, a method for detecting defect in bottle according to a second embodiment of the present invention will be described with reference to FIG. 11. The second embodiment of the present invention is directed to a method for detecting a longitudinal streak in a barrel portion of a bottle. The inventors of the present application made the second invention directed to a method for detecting the longitudinal streak by utilizing a preprocessing function of the first invention described above.

Figure 11:
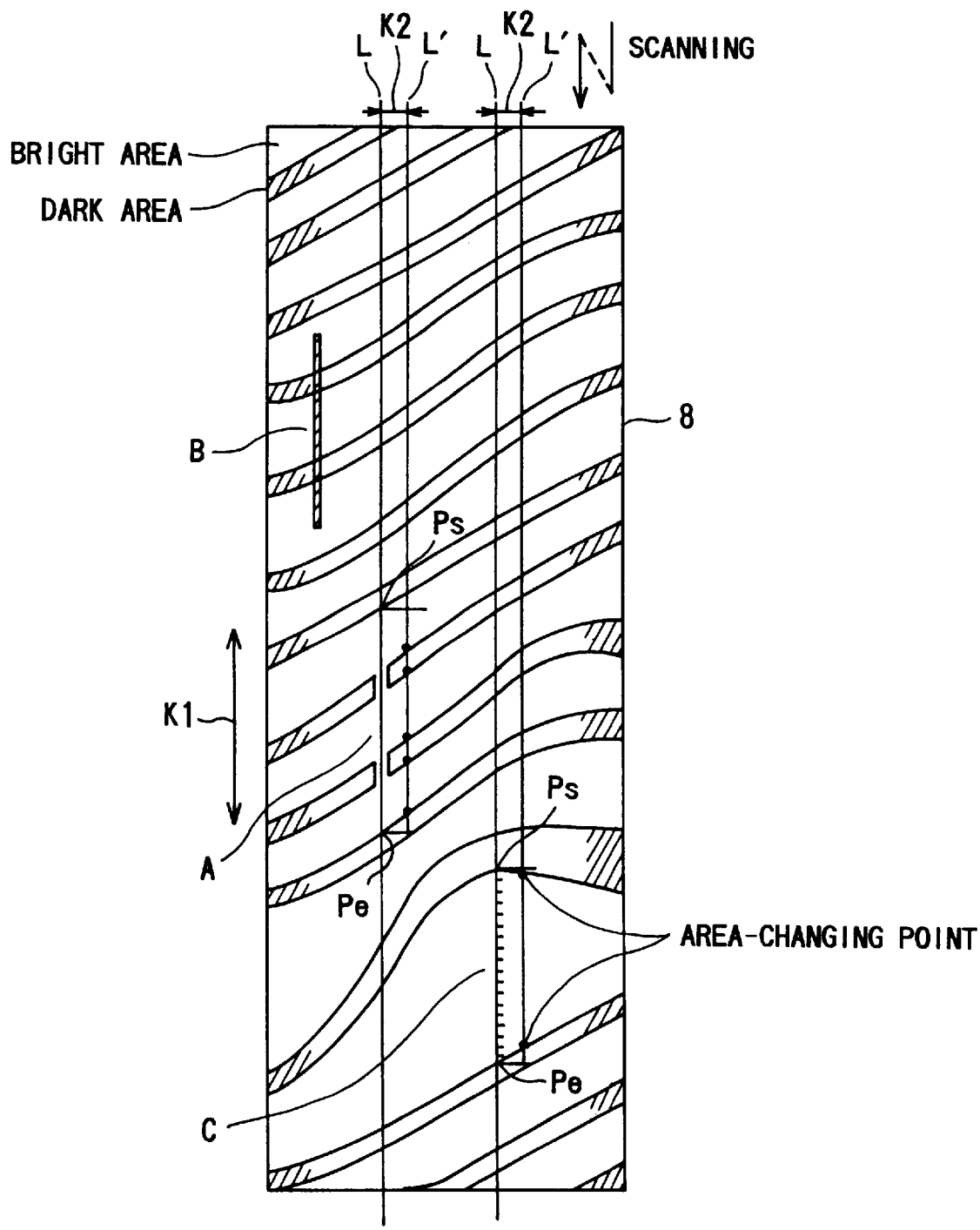
FIG. 11 is a view of a binary image generated by a binarizing process in a second embodiment of the present invention.

FIG. 11 shows a binary image generated by the above binarizing process shown in FIGS. 1 through 4B. That is, the binary image shown in FIG. 11 is generated from the striped pattern in the window 8 of the image 7 through the step 1. In FIG. 11, the image is scanned downwardly from the origin at an upper right corner thereof, and scanned horizontally from the right to the left. In FIG. 11, dark areas are shown hatched only in edge portions, but not in a central portion, of the window 8 for the convenience of illustration.

In step 2, the binary image generated in step 1 is scanned in the longitudinal direction of the bottle to determine the number of successive pixels in bright or dark areas along a scanning line L. In the original image captured by the CCD camera, a longitudinal streak is represented by a succession of pixels which are of an intermediate shade between the dark and bright areas and extend beyond the ordinary distance between adjacent stripes. In the binary image, as shown in FIG. 11, depending on the brightness in the original image, the longitudinal streak is represented by a longitudinal succession of bright or dark pixels as indicated in an area A or B. This is because the longitudinal streak is not a simple recess but a recess around which ridges are formed, and the surface of the streak has an arcute angle, differently from the thin blister. Therefore, the streak forms image of a portion around the streak thereon to cause an area corresponding to the streak to become an intermediate shade between dark and bright areas which is converted into either a bright area or a dark area in the binary image.

If there is a scanning line along which there is a succession of pixels which extend beyond the ordinary distance between adjacent stripes, then there is a longitudinal streak along the scanning line. The number of successive bright or dark pixels is determined along the scanning line L. However, as indicated by an area C in FIG. 11, there is an instance where bright pixels are successively present as with the area A though no longitudinal streak is actually present in the area C.

In step 3, if the number of successive pixels determined in step 2 exceeds a preset number K1, then along a scanning line L' that precedes the scanning line L by a preset number K2, the number of area-changing points where a bright area changes to a dark area or a dark area changes to a bright area is determined between a start point Ps and an end point Pe of pixels which are equal to the successive pixels whose number has exceeded the preset number K1 along the scanning line L. In FIG. 11, the number of area-changing points in the area A is 5, and the number of area-changing points in the area C is 2.

Then, in step 4, if the number of area-changing points determined in step 3 is equal to or greater than the preset number K3, then a defect is determined. In an example of FIG. 11, if the preset number K3 is 3, then the area A (defective area) and the area C (no defective area) are distinguished from each other.

Since binary images generated from bottles vary from bottle to bottle, the preset numbers K1 through K3 are determined as the results of many sample tests, and may be changed if necessary.

The method for detecting defect in bottle according to the second embodiment of the present invention is capable of reliably detecting longitudinal streaks in the bottle barrel as it extracts features of longitudinal streaks in binary images of the bottle as distinguished from stripe irregularities.

Although a certain preferred embodiment of the present invention has been shown and described in detail, it should be understood that various changes and modifications may be made therein without departing from the scope of the appended claims.

What is claimed is:

1. A method for detecting a defect in a bottle, comprising:
    imaging a barrel portion of a bottle with a CCD camera based on light which has passed through a light shield plate having a plurality of oblique slits and said barrel portion;
    generating from an image generated by the imaging step a binary image having a striped pattern of bright and dark striped areas within a window having a certain area;
    scanning said binary image in a longitudinal direction of said barrel portion to generate a labeled image in which labels are assigned to the bright and dark striped areas of the striped pattern, respectively; and
    scanning said labeled image in a longitudinal direction of said barrel portion and determining a defect in said barrel portion if there is a striped area of one label which is not in contact with any one of sides of said window or if a striped area of one label appears more than a preset number of times along a scanning line.

2. A method for detecting a defect in a bottle, comprising:
    imaging a barrel portion of a bottle with a CCD camera based on light which has passed through a light shield plate having a plurality of oblique slits and said barrel portion;
    generating from an image generated by the imaging step a binary image having a striped pattern of bright and dark striped areas within a window having a certain area;
    scanning said binary image in a longitudinal direction of said barrel portion and determining a number of successive bright or dark pixels along a first scanning line;
    determining, if the determined number of successive bright or dark pixels exceeds a first preset number, a number of area-changing points within said window where one of the bright striped areas changes to one of the dark striped areas or one of the dark striped areas changes to one of the bright striped areas along a second scanning line which precedes said first scanning line by a second preset number between a start point and an end point of pixels, wherein the number of pixels is equal to the number of successive bright or dark pixels; and determining a presence of the defect if the determined number of area-changing points is equal to or greater than a third preset number.

* * * * *